US012042340B2

(12) United States Patent
Zannoli (10) Patent No.: US 12,042,340 B2
(45) Date of Patent: Jul. 23, 2024

(54) METHOD AND SYSTEM FOR THE IDENTIFICATION AND HANDLING OF EVENTS IN A SYSTEM FOR THE SYNCHRONIZATION AND COMBINED DISPLAY OF INFORMATION

(71) Applicant: SPARKBIO S.R.L., San Lazzaro di Savena (IT)

(72) Inventor: Sebastiano Zannoli, Bologna (IT)

(73) Assignee: SPARKBIO S.R.L., San Lazzaro de Savena (IT)

( * ) Notice: Subject to any disclaimer, the term of this patent is extended or adjusted under 35 U.S.C. 154(b) by 370 days.

(21) Appl. No.: 17/432,616

(22) PCT Filed: Feb. 25, 2020

(86) PCT No.: PCT/IB2020/051606
§ 371 (c)(1),
(2) Date: Aug. 20, 2021

(87) PCT Pub. No.: WO2020/174398
PCT Pub. Date: Sep. 3, 2020

(65) Prior Publication Data
US 2022/0133430 A1 May 5, 2022

(30) Foreign Application Priority Data
Feb. 26, 2019 (IT) .................. 102019000002737

(51) Int. Cl.
*A61B 90/00* (2016.01)
*G06V 30/148* (2022.01)
(Continued)

(52) U.S. Cl.
CPC ............ *A61B 90/37* (2016.02); *G06V 30/153* (2022.01); *G16H 30/20* (2018.01); *G16H 30/40* (2018.01); *G06V 2201/031* (2022.01)

(58) Field of Classification Search
CPC ........ A61B 90/37; G16H 30/40; G16H 30/20; G06V 30/153; G06V 2201/031
See application file for complete search history.

(56) References Cited

U.S. PATENT DOCUMENTS

| 10,631,811 B2 | 4/2020 | Volkov et al. |
| 2008/0058963 A1 | 3/2008 | Garibaldi et al. |

(Continued)

FOREIGN PATENT DOCUMENTS

| WO | 2016/014384 A2 | 1/2016 | |
| WO | 2016/092503 A1 | 6/2016 | |
| WO | WO-2016092503 A1 * | 6/2016 | ........... A61B 5/7289 |

OTHER PUBLICATIONS

Simona Anzivino, "Studio Di Un Modulo Software Per L'Acquisizione Simultanea Di Segnali E Immagini in Ambito Neurofisiologico—Tesi in Sistemi Neurali LM", Dec. 20, 2012, Universita Di Bologna Sede Di Cesena Seconda Facolta Di Ingegneria Con Sede a Cesena Corso Di Laurea Magistrale in Ingegneria Biomedica, Cesena, Italy. 76 pages (see specification at p. 3, line 24 through p. 4, line 16).

(Continued)

*Primary Examiner* — Gerald Johnson
(74) *Attorney, Agent, or Firm* — Ware, Fressola, Maguire & Barber LLP (57) ABSTRACT

A method and system for the identification and treatment of events for synchronization and combined display of information in a sequence of frames relating to the progress of a diagnostic investigation or surgery performed on a patient. Frames are searched for the occurrence of an event, the search carried out by comparison between identified events and sought-after events, the latter stored in an archive; in the event of recognition of an event, executing a computer program for carrying out a treatment on the frame and/or the activation of a program procedure for signaling the occurrence of the event;

(Continued)

memorizing the event or the frame that contains it, in the correct temporal reference with respect to the sequence of frames.

10 Claims, 5 Drawing Sheets

(51) Int. Cl.
  *G16H 30/20* (2018.01)
  *G16H 30/40* (2018.01)

(56) References Cited

U.S. PATENT DOCUMENTS

| | | |
|---|---|---|
| 2014/0267549 A1 | 9/2014 | Pinter et al. |
| 2016/0224195 A1* | 8/2016 | Okabe .................. G06F 3/0482 |
| 2017/0258526 A1 | 9/2017 | Lang |
| 2018/0153632 A1 | 6/2018 | Tokarchuk et al. |
| 2018/0263574 A1 | 9/2018 | Zannoli |

OTHER PUBLICATIONS

International Search Report, PCT/IB2020/051606, filed Feb. 25, 2020, mailed May 13, 2020, 4 pages.
Written Opinion of the ISA, PCT/IB2020/051606, filed Feb. 25, 2020, mailed May 13, 2020, 8 pages.

* cited by examiner

*Fig. 1 (Known Art)*

Fig. 2 (Known Art)

METHOD AND SYSTEM FOR THE IDENTIFICATION AND HANDLING OF EVENTS IN A SYSTEM FOR THE SYNCHRONIZATION AND COMBINED DISPLAY OF INFORMATION

TECHNICAL FIELD

The present invention relates to the electromedical equipment sector for monitoring the physiological parameters of patients undergoing surgery, or for diagnostic investigations, and in particular concerns a system for the collection and display of synchronized signals from different instruments and equipment used by operators for therapeutic or monitoring purposes.

In the following the present invention will be described and claimed preferably with reference to the surgical or diagnostic medical environment, for the sake of simplicity and clarity, but it must be understood that this is for example only and does not imply any environmental or functional limitation as regards its application.

BACKGROUND ART

As is known, in the course of a surgical intervention, in the operating room there are many devices with different functions, for example a surgical robot, an angiographic arch for carrying out a radiological investigation, a polygraph or multiparametric monitor which allows to display different corresponding signals, for example, to an electrocardiogram or blood pressure, or an eco-doppler instrument or device programmers, used to define the functionality of devices installed on the patient during the procedure or after the surgery, for example a pacemaker or an external ventricular assist pump.

Each of these devices produces its own series of information that relates to one or more parameters correlated with the patient's status, and in particular to the progress of the physiological ones which must be kept under constant control during the intervention. This information, used for the control of certain functions, is generally represented graphically, transformed into representative numeric values, displayed in the form of constantly updated images, and stored in the memory media present within the individual equipment or in another way, by means of devices connected to them.

For standardization needs, the information is transformed into suitable formats, such as those known with the abbreviations "DICOM" or "HL7", which allow for easy storage in large memory containers, also shared among all the equipment. This operation allows one to form many separate files collected in a single large memory device, but does not allow one to check the value or trend of a parameter when, based on the information obtained from another equipment, a certain event.

Technical Problem

In more explicit terms and by way of example, it would be of particular utility, for the surgeon or for those in charge of monitoring the patient's status, to see, for example, how the situation detected by the ultrasound image evolves simultaneously with the progress of the electrocardiogram. Again by way of example, if a certain pathological event affecting the heart is highlighted by the electrocardiogram, it could be useful, for the purposes of determining the cause of the event, to check the condition a posteriori, through the archive, at that precise moment of patency of the blood perfusion system of the heart muscle through the evaluation of the angiographic image, obtained by the radiological system.

To carry out this check with conventional systems, it would first be necessary to recover the electrocardiogram trace and identify the exact temporal position in which the pathological event occurred. Then the moment corresponding to the temporal position of the electrocardiogram should be identified in the sequence of angiographic frames, with the assumption that the timing of the angiographic survey corresponds perfectly to that of the electrocardiogram, a condition almost never verified in operational reality.

This example can be extended to any other physiological or event parameter, pathological or non-pathological, always finding the same problem of recovering and synchronizing the various signals with the necessary precision.

Another need that is evident in the operating environment of an operating room, but also in other areas where complex diagnostic investigations are carried out, is to have the various parameters and significant physiological data of the patient under control, taken from the various instruments, at the same time. as they are acquired, with the possibility of seeing and evaluating these parameters and data simultaneously in a single display, and possibly carrying out on the same operations aimed at highlighting particular situations, always keeping memory of the moment in which they occurred.

It is known the existence, also in the medical-surgical field, of systems that allow the acquisition of signals coming from the main or auxiliary analog outputs, of one or more electromedical instruments, in a specialized computer, in order to memorize and carry them out processing on the same signals and providing useful information about them.

The publication "*STUDIO DI UN MODULO SOFTWARE PER L'ACQUISIZIONE SIMULTANEA DI SEGNALI E IMMAGINI IN AMBITO NEUROFISIOLOGICO*" published 20 Dec. 2012, created as a thesis by SIMONA ANZIVINO, discloses an apparatus of this kind, known under the trade name "LIGHT". This equipment essentially comprises a plurality of analog-digital converters, intended to acquire information relating to the amplitude of the signals output from dedicated signal lines of different instruments used for neurophysiological tests and to digitize them. A computer equipped with an adequate number of digital inputs and a special analysis software provides to perform on each physiological parameter acquired clinical, statistical and correlation analyzes between the different physiological parameters, according to the diagnostic evaluations that must be carried out on a patient.

The apparatus described above in substance, as regards the visualization of the data, behaves in a substantially identical way to a normal polygraph, simultaneously displaying on a monitor the traces acquired in graphic form and printing reports of the analyzes carried out on the acquired signals. Any footage captured with environmental cameras is displayed on a separate monitor. In this regard, it is recalled that a polygraph is an instrument designed for the detection, acquisition and simultaneous display of neurophysiological and cardiovascular signals, such as blood pressure, ECG (electrocardiogram), EEG (electroencephalogram) and respiratory activity.

U.S. Patent Application No. US2008/058963 (Garibaldi et al.) Instead addresses a different technical problem, and describes a unified interactive control device for the operation of various electromedical equipment. In this regard, the device provides a monitor in which it is possible to select the display of what at that moment shows a particular device on its screen, while what is displayed in the other equipment is substantially reduced to icons arranged in inactive areas of the monitor.

However, the equipment described above does not allow to satisfy the needs indicated above, as their functions are dedicated to processing and storing the quantitative characteristics of the individual parameters acquired (Anzivino) or to improve the control of the operation of the individual equipment (Garibaldi).

Significant progress in the ability to integrate information from a set of electromedical instruments and equipment into a single monitor immediately accessible by the operator, and above all synchronization and subsequent combined management of this information, has been achieved with the invention described in the application. International patent published at WO2016/092503A1, in the name of the same Applicant (see US patent application publication number 2018/0263574 for the US National Stage thereof).

Figure 1:
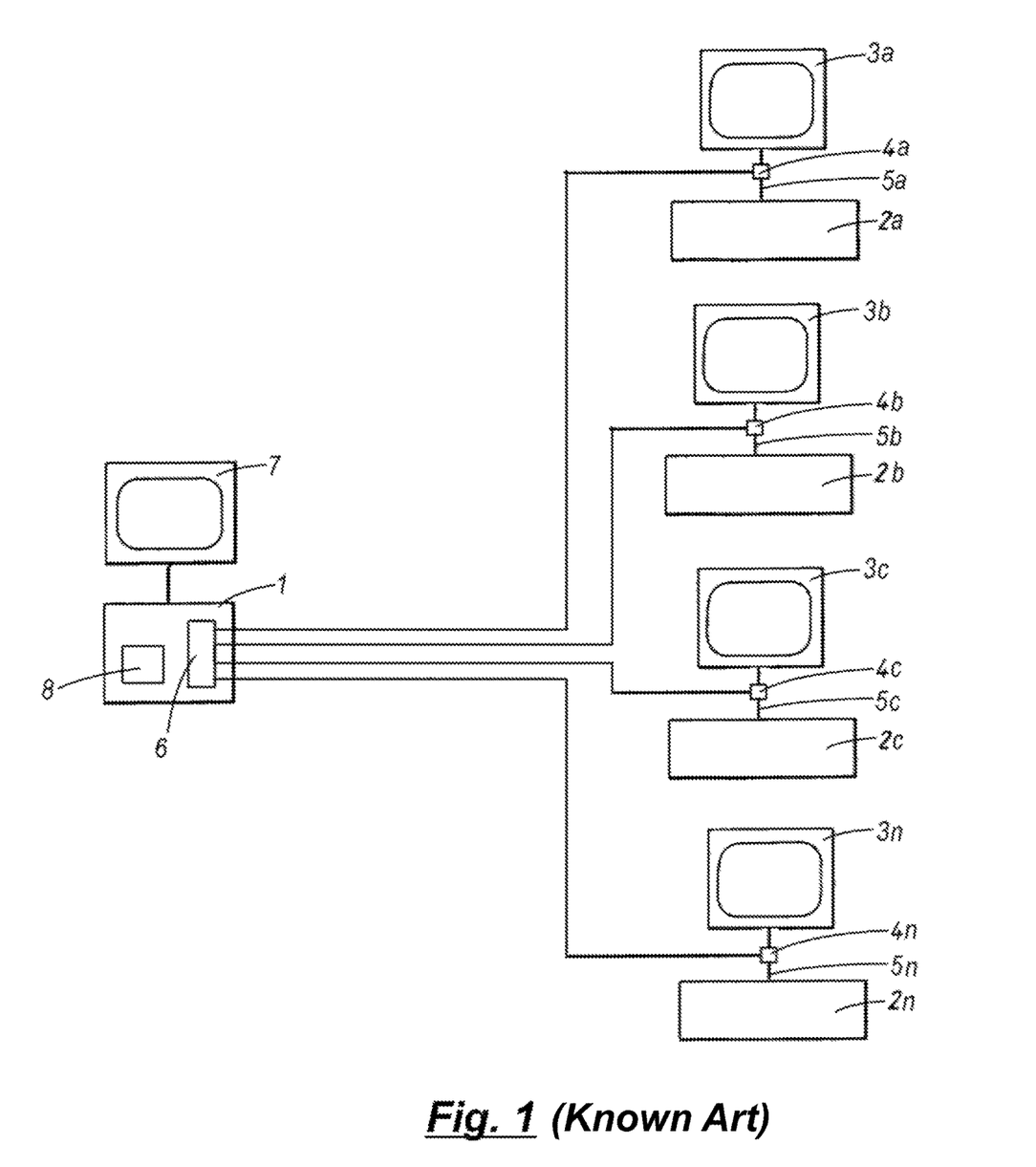
FIG. 1 (prior art) represents a simplified block diagram of the system for the synchronization and the combined display of information, of which the invention constitutes an improvement.

This application discloses a system for the combined acquisition and display of output signals from a set of different electromedical instruments and equipment, and for the synchronized storage of the same signals (see FIG. 1).

Figure 2:
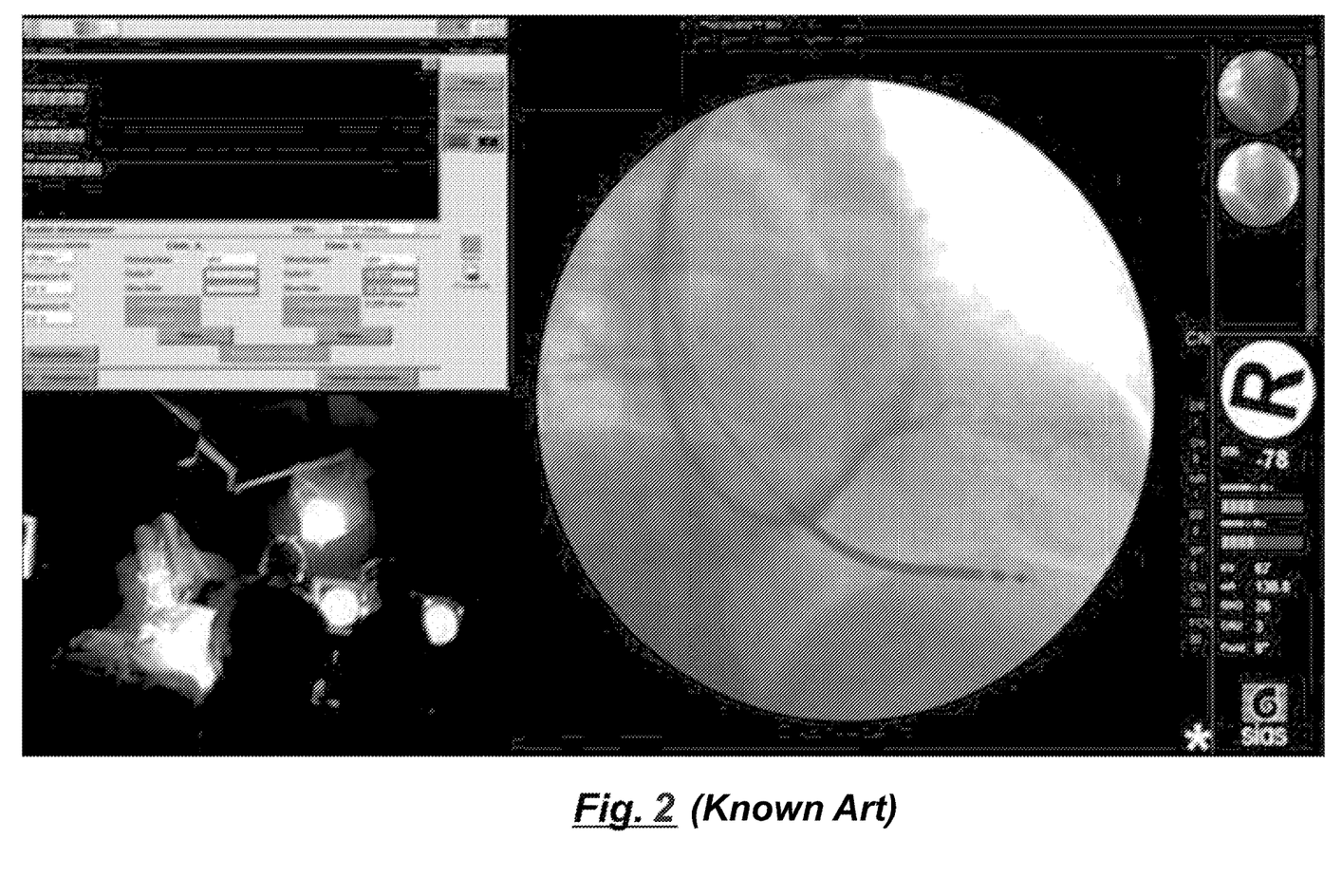
FIG. 2 (prior art) represents a possible frame (frame) combined and subsequently memorized by the system of FIG. 1.

The aforementioned signals refer to the progress of the corresponding physiological parameters of a patient, or to images or videos taken during a diagnostic examination or an intervention carried out by an operator—usually a surgeon, but in some cases also a specialized technician—or by a team of operators (FIG. 2).

In particular, the system comprises video signal or data line derivative devices, each installed in the output connection section of a relative instrument or equipment with the relative displays, to make the video or data outputs available.

The derived signals converge towards a central unit for the collection and processing of the signals, consisting of a dedicated computer in which a management program operates. The latter includes signal acquisition and transcoding procedures, combined visualization procedures in a single monitor available to the operator, insertion of time references to identify significant situations and events of the diagnostic examination procedure or of the intervention in progress, and combined signal archiving procedures, including synchronization and time reference information. The program also includes operator interface and input/output procedures, to manage a sufficient number of input information channels to integrate and synchronize all the most important instruments and equipment used in the most common diagnostic and interventional procedures being performed in the room. In which the procedures are operating.

The system described above allows the operator who carries out the diagnostic examination or the intervention, first of all to have in a single screen all the information coming from the equipment and instruments of the room, both in the form of images or video footage and in the form of strings of numeric data; secondly, it allows him to insert temporal references ("markers") in correspondence with situations of interest, or topical events, of the current intervention or exam, and to synchronize with these references all the information collected for that diagnostic exam or intervention.

In this way the operator has available, on a single monitor, all the information useful for the operation he is carrying out, in the form of windows of different sizes which represent the video outputs of some equipment, for example a surgical robot and an arch angiography, and contextually information in the form of alphanumeric strings from other equipment, for example the physiological parameters received by the multiparametric polygraph (systolic and diastolic pressure, oxygen saturation, etc).

The display of this information can be manipulated, i.e. the windows that represent it can be enlarged, to bring them to the foreground and in a central area of the monitor, if in a certain phase of the surgery in progress they are particularly interested to observe; or they can be reduced and displayed in a peripheral area of the monitor, if in that phase it is the information coming from another equipment that is considered to be more important.

The possibility of inserting a time reference at any time, which is associated with all the information acquired in that instant, provides the operator with an additional tool to find and subsequently view topical moments of the surgery, having all the information immediately available in the form of significant video and/or text. This allows one to easily find all the information relating to the aforementioned topical moments, both during the surgery itself and later, when the surgery is completed. In particular, this feature is particularly advantageous if the operator is interested in analyzing these moments in detail, or if he intends to use the filming of the surgery for educational or information purposes, for example during a lesson or a report at a conference or specialist seminar.

Although the combined acquisition, synchronization and visualization system described above constituted a significant progress in the management, and above all in the usability, of the data and information acquired during a diagnostic exam or surgery, it does not address, and therefore does not solve, aspects relating to the identification and automatic, or semi-automatic, treatment of situations or information of particular interest that may occur, in a certain way or with a given probability, during the execution of the diagnostic or intervention investigation operation.

In particular, these situations or information may relate to purely technical aspects and, for example, relate to a particular feature present in one or more video images acquired by the system and displayed on the monitor, or in an alphanumeric data sequence; or it may concern aspects relating to the protection of the patient's privacy subject to the diagnostic investigation or intervention.

As regards the latter aspect, the privacy regulations (for example, the EU directive 2016/679) impose particular constraints on the processing and disclosure of personal data, also and above all in the health sector.

The problem arises evidently for the personal data processed during surgical interventions and diagnostic investigations. In order to allow the correct storage and subsequent management of information on central archiving systems ("PACS"), it is essential that the references of the particular patient are present in all the monitoring systems used.

On the other hand, it is clear that, as long as these data are confined in the hospital setting, there is no violation of patient privacy. If, on the other hand, the data relating to the monitoring of the intervention, including images, videos and numerical data relating to the patient's physiological parameters, must leave this area, to be used, for example, for educational or illustrative purposes, the problem of the confidentiality of these data it is clearly and, at present, difficult to solve.

OBJECTS OF THE INVENTION

The main object of the present invention is to propose improvements to the system for the acquisition, synchronization and combined display of data and information coming from the monitoring of a diagnostic investigation or an intervention, as previously described, which allow to solve the problems listed above.

In particular, an object of the invention is to propose a method for the automatic and semi-automatic identification and treatment of situations or information of particular interest which can occur, in a certain way or with a given probability, during monitoring the execution of a diagnostic investigation or surgery.

Another object of the invention is to propose a system, based on computer program procedures, for carrying out the process described above.

SUMMARY OF THE INVENTION

These and other objects will be obtained by the method and the system which are the object of the present invention, realized in accordance with the description below.

The invention consists of a method, and a related system based on processing program procedures, intended for the identification and treatment of events in a main system for synchronization and combined display of information relating to the progress of a diagnostic investigation or surgery performed on a patient. The method and the system are part of the aforementioned main system for displaying and synchronizing this information.

The information consists of output signals from electro-medical instruments and equipment, and relates to the progress of the patient's physiological parameters, or to a sequence of images or videos taken during the course of the diagnostic investigation or intervention.

The method includes the execution, on each frame belonging to said sequence, or belonging to at least a predefined set of frames of said sequence, of the following operating steps:
  the search, in the frame, for the occurrence of at least one event, the latter including the presence of a character or sequence of characters, or a graphic form;
  examples of such characters or graphic form being stored in an archive in the central unit of the main system; the search is carried out by comparison between identified events and sought-after events, the latter comprising at least one of the aforementioned events stored in the archive;
  in the event of recognition of at least one event, for each recognized event, the execution of a program procedure for computer capable of carrying out a treatment on the frame and/or the activation of a program procedure for computer capable of signaling the occurrence event;
  the memorization of the event, or of the frame that contains it, in the correct temporal reference with respect to the aforementioned sequence of frames.

BRIEF DESCRIPTION OF THE DRAWINGS

The characteristic features of the invention which do not emerge from what has been said above are highlighted in the following description, with reference to the accompanying drawings, in which.

DESCRIPTION OF PREFERRED EMBODIMENTS OF THE INVENTION

With reference to FIGS. 1 and 2, a system 100 for the acquisition, synchronization and combined display of data and information coming from the monitoring of a diagnostic investigation or an intervention is illustrated. In particular, the system allows the acquisition, synchronization and viewing on a single monitor 7 of the output signals, video or data, coming from a set of instruments and equipment 2a, 2b, 2c, . . . 2n, normally used in the room. operative during a surgical intervention or a diagnostic investigation, for example an angiography, performed on a patient.

As mentioned in the introduction, in this discussion reference will be made to the specific environment of an operating room, but this must not be seen as a limitation, since the invention can also be validly applied in other similar areas, or which in any case have identical or similar needs.

Still by way of example, and not with a limiting function, it is specified that the set of different instruments and equipment 2a, 2b, 2c, . . . 2n may include, among others, a surgical robot, an angiographic arch and/or a polygraph o multiparametric monitor, and/or a thoracic strain-gage, and/or an eco-doppler console, and/or a series of programmers for medical devices and all the instruments for monitoring and anesthesiological and respiratory support. The list is obviously not exhaustive, and in any case only a part of the instruments and equipment listed can be provided.

Each of the instruments and each of the equipment 2a, 2b, 2c, . . . 2n comprises means for displaying images 3a, 3b, 3c, . . . 3n representative of the progress of one or more physiological parameters of the patient, or of an image of a part of the body or of an apparatus of the same patient, acquired during an intervention. It should be noted that these images are generally taken as a continuous film or video, with a shooting rate comprised between a few frames per second and a few tens of frames per second. For the purposes of the present invention, reference will be made to this video as "image", to indicate a single frame ("frame", according to the commonly used technical terminology), or "image sequences" to indicate a continuous succession of frames, which make up the aforementioned video or clips of it.

In particular, moreover, the display means 3a, 3b, 3c, . . . 3n consist of a monitor, suitable for receiving and displaying video signals received at the input, for example according to the VGA or other video format standard (FIG. 1), such as a composite video, DVI, HDMI, etc.

The VGA or other video format monitors are connected to the video outputs of the instruments and equipment 2a, 2b, 2c, . . . 2n, according to appropriate cables.

It is understood that, in the equipment or instruments 2a, 2b, 2c, . . . 2n which can be used for the system according to the invention, the video monitors can also be integrated, provided that they are equipped with a direct video output line, of the VGA or other type industrial video standard (as already mentioned, for example a composite video, a DVI standard, HDMI etc.) In the following we will refer to the VGA standard, but only as an example.

For the purposes of the invention, among the possible video sources, the video outputs from all the equipment and instruments present in the operating room, such as angiographs, ultrasounds, etc., as well as from environmental cameras are to be ascribed, by way of example and without limitation possibly present in the operating room, with the possibility of zooming in on the intervention area.

In order to avoid any conditioning of the standard operation of the room, in the connection section 5a, 5b, 5c, . . . 5n of each of the aforementioned instruments and equipment 2a, 2b, 2c, . . . 2n with the relative display means 3a, 3b, 3c, 3n as many analog video signal derivative devices 4a, 4b, 4c, . . . 4n are installed, in particular of the VGA or other video format splitters, of a type normally available on the market.

One of the outputs of each splitter 4a, 4b, 4c, . . . 4n is connected again to the monitor of the relative instrument or relative equipment, so as to restore the previous normal operation.

A plurality of branch connections 5a, 5b, 5c, . . . 5n connect the other outputs of the analog video signal splitters 4a, 4b, 4c, . . . 4n to a central unit 1 for collecting and processing the signals. The central unit 1 comprises means, devices and memories for the execution of processing programs suitable for the functions that it must perform, as will be evident in the following.

In particular, the branch connections 5a, 5b, 5c, . . . 5n are connected to video acquisition cards or channels 6, capable of capturing the signals in the format produced by the equipment 2a, 2b, 2c, . . . 2n, for example the format VGA, and to store them in special memory areas provided in the central unit 1. These acquisition cards, commonly available on the market and provided with a number of acquisition channels at least equal to the number of connections 5a, 5b, 5c, . . . 5n, they are also installed in the central unit 1. In this way, the split signals received are each transformed into sequences of digital images, for each of which a time reference is defined. Each sequence of images (frames) relating to each acquisition channel is stored in corresponding video files, according to completely known techniques, which preferably bear associated information relating to the acquisition time.

By means of a suitable processing program, residing and operating in the central unit 1, the digital images obtained are then combined into a single image, to obtain corresponding composite images, in which two or more of these digital images are suitably arranged in a combined image, depending on the viewing scenarios defined by an operator. The combined image is then reproduced on display means 7, which identify themselves in a monitor connected with, or integrated into, the aforementioned central unit 1.

The operation described above is repeated continuously for each frame acquired at the same time by the different acquisition channels, in order to obtain on the monitor 7 output a continuous movie in real time which shows the shots taken by the equipment or instruments 2a, 2b, 2c, . . . 2n selected in the currently defined scenario (see FIG. 2). A scenario modification procedure is provided to allow the operator to change the displayed scenario at any time and replace it with different scenarios that may have been previously defined or currently defined.

In the event that the different video signal sources operate at different screen reproduction rates ("frame-rate"), the software procedure for acquiring the signals with lower frame-rate conveniently duplicates a frame of the relative video so as to obtain, per unit of time, a constant number of frames for all the sources acquired and reproduced on the monitor 7.

For each scenario displayed on monitor 7, through a selection procedure that is part of the processing program, there is the possibility of choosing a favorite image among those that appear in the scenario, and showing it enlarged compared to the others, since at that moment more significant for those who perform the intervention. There is also the possibility for the operator to command the replacement of this preferred image within the scenario with another image of the same scenario.

In other cases, it is possible to review the images in post-processing mode one by one or all at once.

As an example, FIG. 2 shows a combined image displayed in monitor 7, consisting of a scenario comprising the composition of the video output of an X-ray apparatus, a pacemaker programmer and the recording of an environmental video camera placed in the operating room. In this case, the preferred image of the scenario is that provided by the equipment for X-ray scopes.

In the operating room it is therefore possible, for operators who perform an intervention, to check in a single monitor the progress of significant physiological parameters upon the occurrence of certain events detectable by other monitored parameters, and to control all this by simultaneously viewing the image taken by a diagnostic or intervention tool used at that time on the patient. For example, at a time when there is a drop in pressure, it is possible to check the behavior of the heart walls in the ultrasound image, or to detect the other physiological parameters related to a possible variation in pressure.

The possibilities of processing and displaying combinations of various images and shots are very numerous, being able to highlight one, enlarging it or making it more marked than the others that one intends to keep in the background. All these possibilities will be evident and within the reach of those skilled in the art.

In order to keep track of the acquired and displayed images, independent memory means 8 are provided in the central unit for each digital image, or sequence of images, received from each instrument and/or each device 2a, 2b, 2c, . . . 2n. This allows an operator, if he deems it useful, to recall the images or sequences at a later time and analyze them, individually or in any combination between them.

In addition to the aforementioned video signals, the monitor 7 can also display analog or digital data signals from instruments which output values, in analog or digital format, indicative of an amplitude of the monitored physiological parameter.

To make the system more functional, the central unit 1 includes a processing and conversion program, residing on a suitable memory in the central unit 1 and operating via a suitable analog/digital conversion electronic board, for sampling one or more analog signals. This program is able to acquire and convert the non-video outputs of instruments 2a, 2b, 2c . . . 2n into digital format which provide analog signals whose amplitude is correlated to the value acquired in an instant by the parameter or parameters that the program is monitoring. The acquisition and conversion program is also intended to generate corresponding images or image sequences of the value of the aforementioned parameter, or of the aforementioned parameters, suitable for being inserted in the above described combined images.

For example, a polygraph is normally equipped with an output from which it is emitted as a voltage signal corresponding to the electrocardiogram at the same time represented on the relative monitor.

In other cases, an instrument can output an equivalent signal, but with digital coding of the information, according to known protocols. In the latter case, suitable digital input lines are provided in the central unit 1, capable of recognizing and acquiring these digital output signals.

Advantageously, the timing of the sampling of the analog signals can be carried out by using the synchronism signal generated by the sampling board of one of the available video signals, coming from the different devices, as the synchronization signal for the analog/digital conversion card. In this way, each "frame" of the acquired video corresponds to a single sampling of the analog signals. By using this synchronism signal as a reference for sampling analog signals, one is always sure of the perfect synchronism between video and analog channels.

This allows the tracing, together with the superimposed digital images, of a corresponding graph, which shows the real analog values of the monitored physiological parameters, allowing to assign the corresponding values to the images represented, which usually allow instead a more qualitative evaluation.

Furthermore, again to provide the system with greater functionality and information capacity, the processing program includes a character recognition procedure, designed to detect the graphic representation of numeric values representative of a physiological parameter, which are normally reproduced within the related digital images in predefined positions. In practice it is a common OCR program, that is, recognition of alphanumeric characters starting from their graphic representation in a pixel matrix.

The purpose is to obtain a punctual value used individually or in combination with other values, obtained in the same way from other images acquired simultaneously or with the value of the analog signals sampled, to allow further diagnostic evaluations to be carried out, also with reference to the representation in superimposition of the images relating to the various physiological parameters monitored.

For example, if at a particular instant the blood pressure assumes an anomalous value, one can refer to the ultrasound image of that instant to obtain, through the OCR program, the value shown graphically in a given position, usually fixed, the punctual value corresponding to the contractility of the heart wall, and therefore one can identify a relationship between the contractility of the detected heart wall and the abnormal pressure value.

The processing program which manages the functions of the system in the central unit 1 furthermore advantageously comprises a procedure for inserting time "markers" in correspondence with the images relating to significant events of an operating session. These markers can be entered by an operator via the normal input interfaces present in the central unit 1, for example a mouse or a keyboard, both at the time of the occurrence of the significant event, and in a subsequent post-acquisition phase. In correspondence with each marker, the introduction of a comment note may be envisaged, or measurements relating to the analog signals acquired at that moment, or immediately before or immediately after, may be introduced. The markers, and the related notes, are also stored in the mass memory of the central unit 1.

The processing program also includes a procedure for generating video files in a standard format (for example the .AVI format), starting from the combined frame sequences, for the scenario displayed on monitor 7 at all times, and for the whole duration of the diagnostic investigation or intervention.

In addition, the processing program may also comprise an extraction procedure, intended to respond to a particular instruction by an operator. Following this instruction, the procedure extracts a video file from the sequence of combined images during acquisition and storage, lasting between a predetermined prior period and a predetermined back period, with respect to the moment of receipt of the instruction. This video can include, for example, the previous 20 seconds and the 20 seconds following the instruction, to fix and make available later a particular passage of the intervention in progress.

The generated video files can therefore be made available for export and for subsequent viewing on any IT or telematic channel, as a document of the actual progress of the intervention and what the person who made it wanted to view to have the instruments under control of the operating room.

Figure 3:
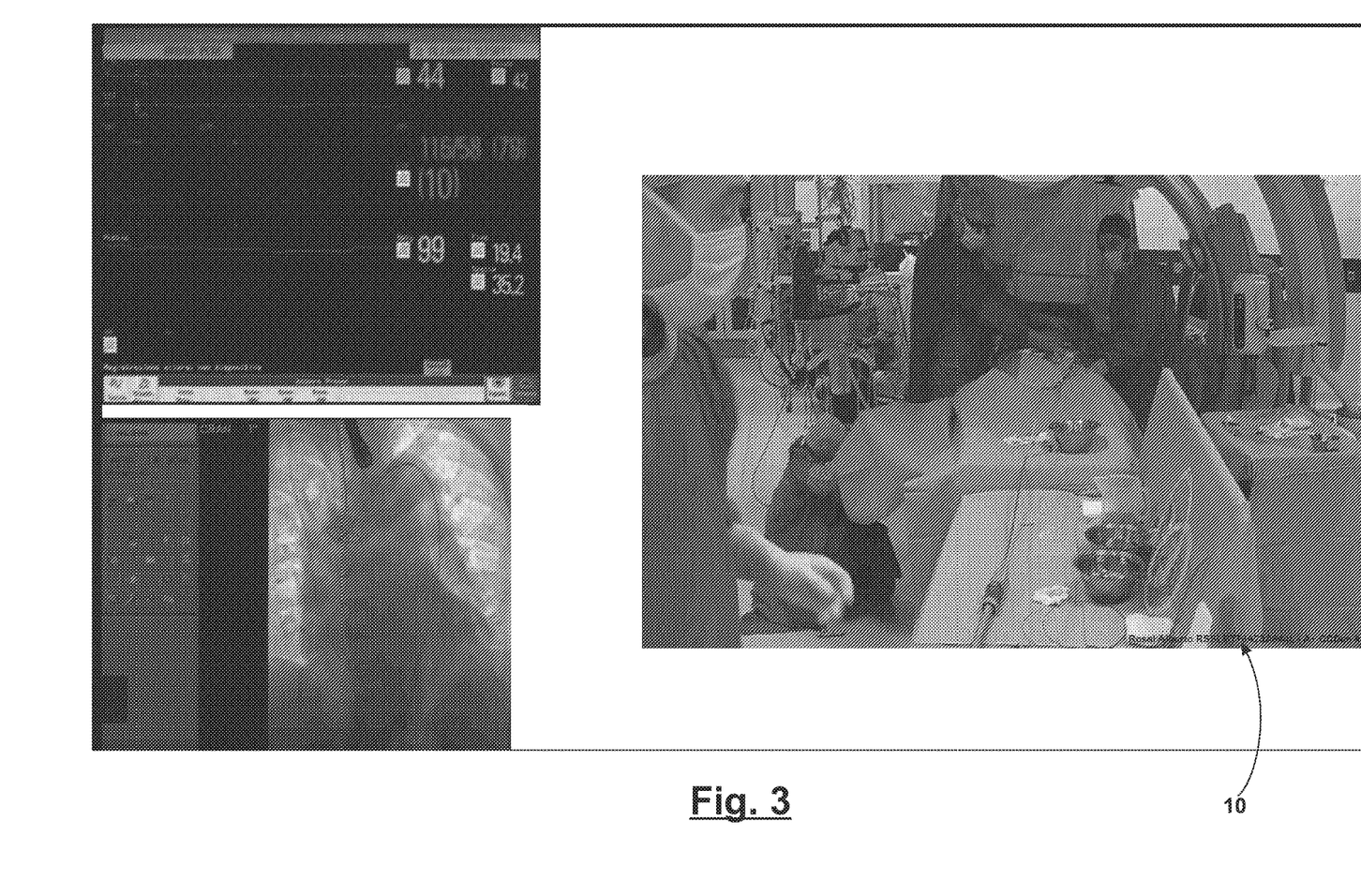
FIG. 3 illustrates a possible combined frame, containing sensitive data of a patient in a viewing window.
Figure 4:
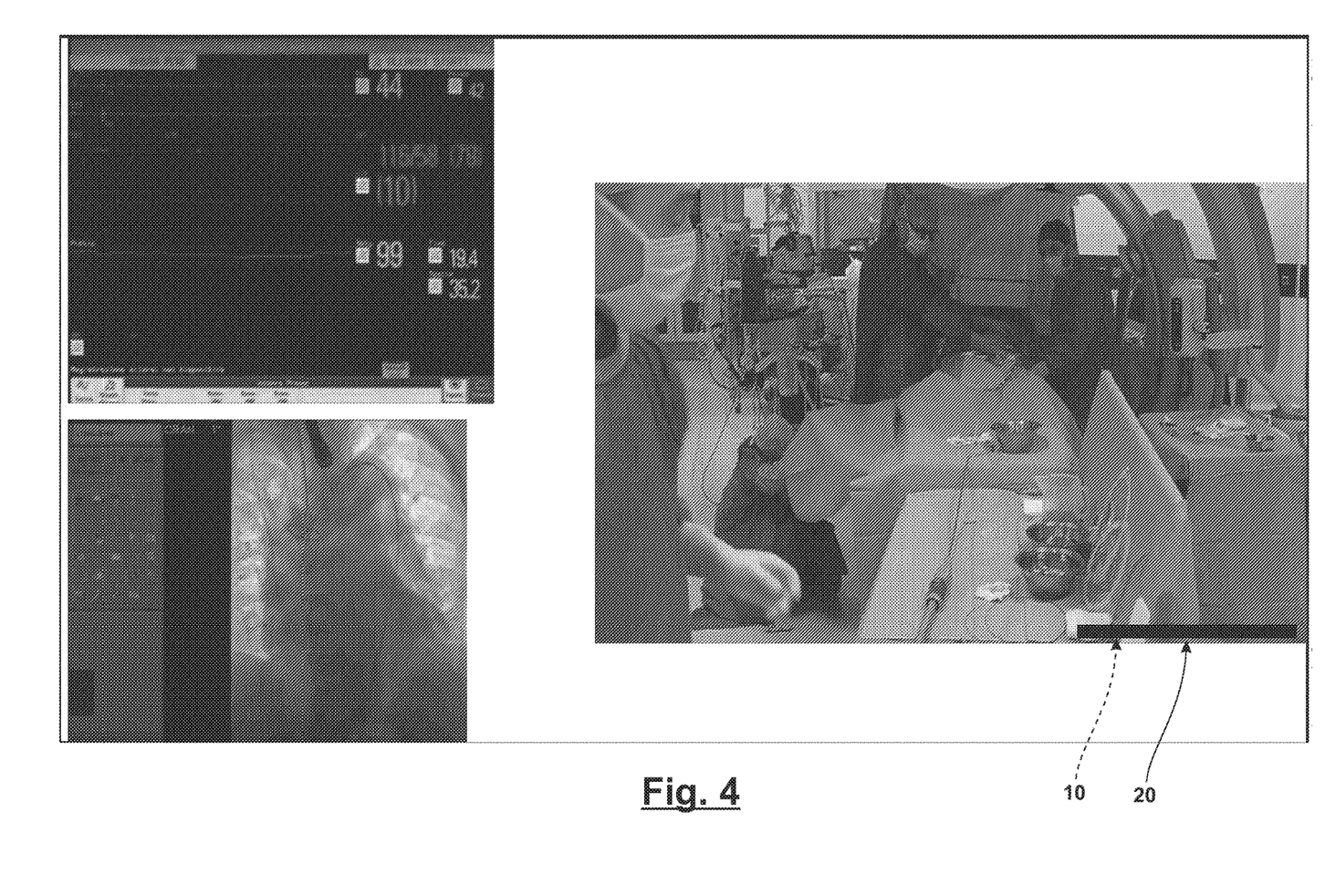
FIG. 4 illustrates the combined frame of FIG. 3, in which the sensitive data have been masked.
Figure 5:
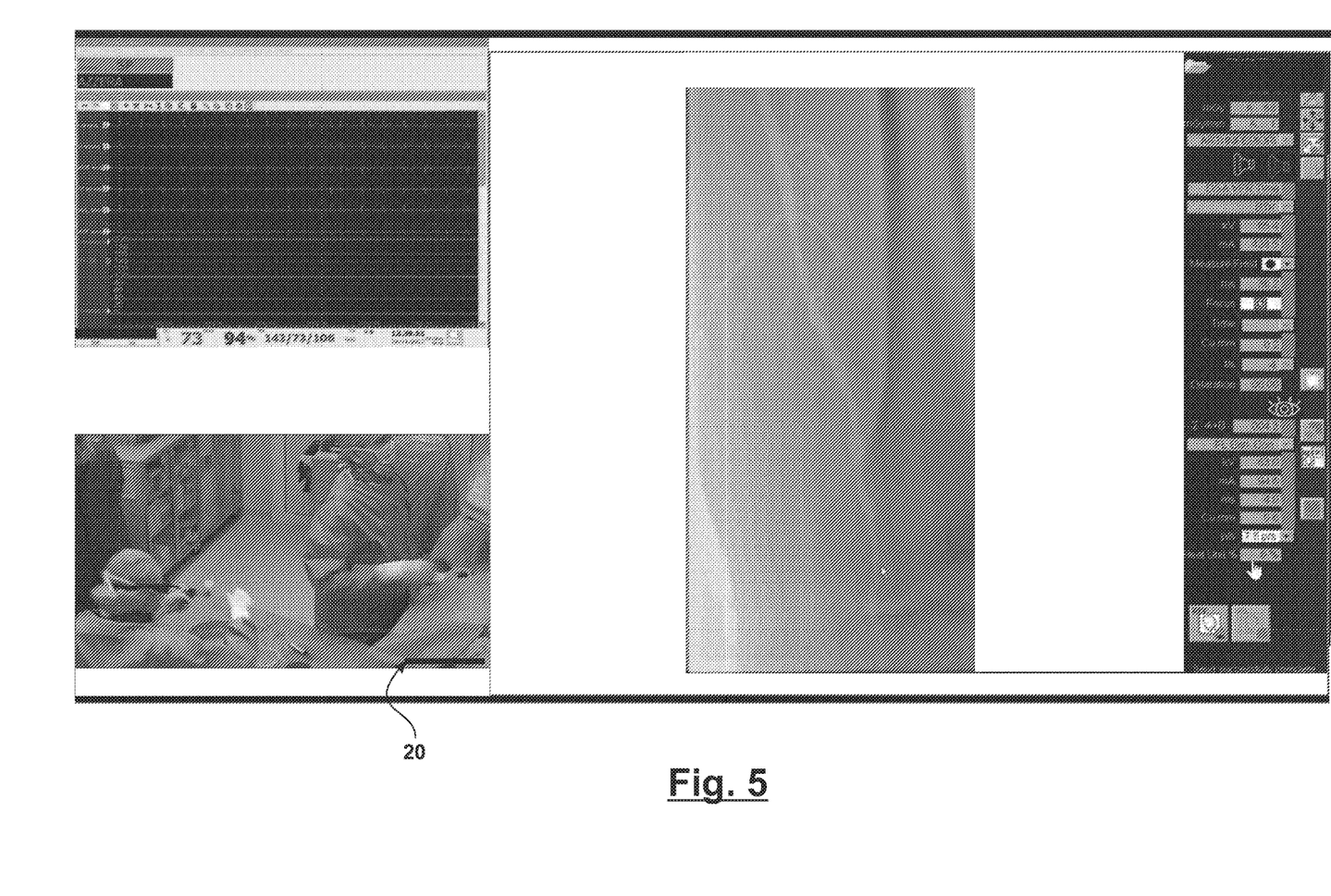
FIG. 5 illustrates a frame with the display windows moved and resized, in which the masking of sensitive data is moved and resized accordingly.

The method for the identification and treatment of events in a system 100 for the synchronization and the combined display of information according to the invention, which will be described below with reference to FIGS. 3, 4 and 5, is part of a system of type of the one illustrated above, but not limited to and exclusively in this system.

The method is preferably carried out within the central processing unit 1, through program procedures integrated in the processing program which manages the acquisition, display and synchronization operations of the output signals derived from the various instruments and equipment, and which generates the combined output of the information to the monitor 7. Depending on particular choices or needs, the method implementation procedures can be equally advantageously performed by a separate processing program, which can be activated by the operator at the appropriate time.

The aforementioned method applies first of all to the sequence of frames (frames) generated by the main processing program and intended to be displayed in monitor 7 and subsequently—or at the same time—stored in a file in the mass memory of central unit 1. In particular, the method can be applied to all the frames subsequently generated by the program, or to a temporally predefined set of frames, or to a sequence of frames not necessarily contiguous to each other.

In order to implement this method, in an instant preceding the start of the diagnostic investigation or of the intervention to be monitored, the operator defines one or more events that he considers significant for the execution and documentation of the investigation or intervention and stores its parameters in a memory area of central unit 1 accessible to the method implementation program. These parameters can be supplied manually, or taken from special databases, according to needs and availability, as will be explained more clearly below.

A first class of events which is certainly of interest for the method according to the invention is constituted by sensitive data 10 of the patient who is the object of the diagnostic investigation or intervention (see FIG. 3), such as for example name, surname, date of birth, tax code, etc. As already anticipated, in fact, these data are generally displayed in the video outputs of different instruments or diagnostic equipment, or must in any case be present to allow the storage and subsequent management of patient information on the aforementioned central archiving systems ("PACS"). However, it is not allowed by privacy regulations, and often it would not be advisable from an ethical point of view, to disclose such information outside the purely hospital, or in any case medical, sphere.

In the combined images displayed on monitor 7, sensitive patient data 10 can be in different areas of the screen at different times and have different sizes. For example, they can be in the window used for a certain period as the main one (FIG. 3) and occupy a certain area of the screen. Subsequently, the same window can be viewed as secondary, and therefore resized and positioned in a different area of the screen (FIGS. 4-5).

A second class of events of interest consists of information, both graphical and alphanumeric, which have a higher or lower probability of appearing in the survey video or intervention displayed on monitor 7 during the surgery, and the occurrence of which may be significant and useful for the operator, both in real time and in a subsequent study or presentation phase of the surgery video. These events can escape the attention of the operator at the moment if not properly monitored; their timely identification can also, in some cases, positively influence the progress of the investigation or intervention. For example, events of this type may be the symbols represented on the screen by some devices connected in correspondence with particular events, such as the start and end of the X-ray emission by angiographic systems.

The method object of the invention manages the two types of events, and other similar types of events, through program procedures for computers, whose practical implementation falls within the skills and capabilities of the technician in the medium experience sector. These procedures intervene on the data generated by the display and synchronization system described above, and in particular on the sequences of frames intended to be displayed on the monitor 7 and/or on the sequences of images output from the instruments and equipment in the operating room and acquired by the the central unit 1 of the system, carrying out on it a series of successive operations which can be summarized in the following operating phases.

For each selected frame, the presence of at least one of the events mentioned above is sought. In particular, sequences of characters or graphic forms having an identifiable profile are sought in the frame.

According to a first embodiment of the invention, in a first operating phase, the identification of the character sequences is carried out by means of a character recognition procedure (OCR). This type of procedure exploits algorithms well known to programmers, which are commonly used to convert text written in raster format files into code.

Following the identification of a sequence of characters, a second phase of the method is activated, which consists in comparing the identified sequence with one or more sequences, relating to the patient's sensitive data 10 (for example name, surname, tax code, etc.), among those archived or otherwise previously provided by the operator, to verify correspondence.

In the event that the comparison is successful, a further procedure (or part of the procedure) is activated, whose function is to provide for the identification of the positional coordinates of the sequence on the frame, and therefore to generate a mask 20 to cover the area of this frame which includes personal data, to obtain in the monitor 7 a corresponding masked frame (FIG. 4).

The frame is then displayed on monitor 7 and stored by the main system processing program in the file relating to the combined recording of the diagnostic examination or of the intervention, in the correct time sequence. In this way, the patient's sensitive data is obscured "from the beginning", and can no longer be recovered from the recorded file, in compliance with the strictest privacy protection regulations.

Optionally, in a subsequent operating phase, the procedure also generates a mask for the image, including the patient's sensitive data, acquired by the system as an output of the equipment or instrument that generated it, before saving it. The mask is positioned in the area of the image containing the aforementioned sensitive data. In this way, with each subsequent display of the image, these data are covered and not visible.

According to another option, a further operating phase of the method activates a procedure for changing the spatial coordinates and the size of the mask according to the movements and/or resizing of the window that contains the patient's sensitive data that may be carried out by the processing program following operator instructions, and then displayed in the following frames in monitor 7 (FIG. 5). In this case, said modification procedure interfaces with the main program, detects the extent of the displacements or resizing, calculates the new positional coordinates for the patient's sensitive data and the new dimensions of the cover mask, and applies them automatically to subsequent frames, without there being an intervention of the aforementioned character recognition procedures, comparison and possible generation of cover masks.

A second embodiment of the invention relates to the recognition of events which consist in the occurrence of particular physiological conditions in the patient under investigation or undergoing a surgery (for example, the presence of an embolus in a blood vessel, an incorrect positioning or displacement of a catheter, the presence of a sequence of characters indicating an attention value for a physiological parameter, the achievement of the contrast medium in the radiological investigation area, etc.).

According to the method, in an initial operating phase, the identification of the graphic forms in the frame under examination is carried out by means of other procedures for recognition and isolation of contours, while the possible identification of the sequences of characters is still carried out by means of a character recognition procedure (OCR). Also in this case, the first procedure exploits algorithms well known to programmers, which are commonly used in various sectors of the industry for the recognition of objects starting from their visualization on images.

In the case of identification of a significant event, i.e. a contour or a sequence of characters, a second phase of the method provides for the activation of a procedure (or part of the procedure) for comparison with the models stored in memory. If the outline or the sequence of characters found coincide with one of those present in the archive, a procedure (or part of the procedure) is first activated which generates a visual and/or acoustic signal for the operator. The visual signal can be visualized on the monitor 7, in the form of a text message, of the enhancement of the outline or of the sequence of characters found, or other form.

The emission of the visual or acoustic signal can persist as long as the event continues to be detected in the following frames, or it can be given one-off, and possibly reset by the operator once the operator has acknowledged the occurrence of the event.

At the same time as the issue of the report, a procedure (or part of the procedure) of automatic generation of a positional reference (marker) is activated in the registration file of the diagnostic investigation or intervention, or in any case in the management structure of the registration already in progress. production route by the main processing program of the system.

The implementation of the method described above provides clear advantages for the operator, or the team of operators, engaged in carrying out the diagnostic investigation or the intervention, even beyond those already highlighted for the system for displaying and combining information of which this method constitutes an improvement.

First of all, the method allows one to advantageously eliminate any personal reference to the patient who is the object of the diagnostic investigation or intervention, and therefore to respect the right to privacy of the same, and to comply with all the most stringent regulations on the matter. All this happens without the need for manual intervention by an operator, both in real time and during the subsequent processing of the recorded information.

It is also evident, both for the operator and ultimately for the patient himself, the advantage that derives from the automatic recognition, and immediate reporting, of events related to potential risk situations, or in any case unwanted or unexpected, which can occur during the surgery. In this case, the operator is greatly facilitated in identifying these events, and can pay more attention to the more purely technical aspects of the diagnostic investigation or intervention.

It is understood that the described method can be applied, making appropriate variations which in any case fall within the inventive concept in question, also to other areas and sectors, without departing from the spirit of the invention.

It is also understood that different embodiments or variations of the present method, even if not explicitly described, are understood to be within the scope of protection granted to the present invention as previously described and defined in the following claims.

The invention claimed is:

1. A method for identification and treatment of one or more events in a system for synchronization and combined display of information relating to progress of a diagnostic investigation or surgery performed on a patient, the information consisting of output signals coming from electromedical instruments and equipment (2a, 2b, 2c, . . . 2n), wherein the progress of the diagnostic investigation or surgery relates to at least one physiological parameter of said patient, or to images or videos taken during said diagnostic investigation or surgery, said system (100) comprising video signal derivative means (4a, 4b, 4c, . . . 4n), for deriving said image or video and providing derived output signals; a central unit (1) for collecting, processing and displaying the derived output signals; a processing program, operating in said central unit (1), comprising procedures for processing, displaying and storing said derived output signals; and acquisition means in said central unit, responsive to the derived output signals for cooperating with said processing program to make the derived output signals available for display in combined form in a monitor (7) of said central unit (1) as a sequence of successive frames suitable for constituting a continuous film or video, and for storage of the successive frames in the central unit (1); said method comprising executing, on each frame belonging to said sequence, or belonging to at least a predefined set of frames of said sequence, of the following operating steps:

searching, in said frame, for identifying occurrence of the one or more events comprising presence a character or sequence of characters (10), or a graphic form, wherein examples of said character or sequence of characters or graphic form are stored in an archive in the central unit (1), said searching carried out by comparing an identified occurrence of the one or more events and sought events for recognizing the identified occurrence as an occurrence of a sought event, the sought event comprising at least one of said one or more events stored in the archive;

executing, in case of recognition of at least one event, for each recognized event, a program procedure for a computer for carrying out a treatment on said frame and/or the activation of a program procedure for a computer for signaling the occurrence of said at least one event; and storing information relating to said at least one event, and/or a frame containing said at least one event, with a temporal reference with respect to the sequence of successive frames, wherein said at least one event consists in personal data of the patient, and said treatment comprises generating a mask (20) covering an area of said frame which includes the personal data, in order to obtain in the monitor (7) a corresponding masked frame, said storing carried out while keeping said masked frame a correct position in time within a temporal sequence with respect to the sequence of successive frames.

2. The method according to claim 1, wherein, if in said monitor (7) the area containing the personal data is moved and/or resized in one or more successive frames by a procedure of said processing program, said procedure also moves and/or consequently resizes said mask (20) in masked frames, to keep the area with personal data covered.

3. The method according to claim 1, wherein said processing program also stores a copy of a corresponding derived output signal comprising said personal patient data, and that said covering mask (20) is also generated and stored in the sequence of successive frames relating to the corresponding derived output signal.

4. The method according to claim 1, wherein the searching for said at least one event that consists in personal data is carried out by an OCR or character recognition procedure in a file of the "raster" type, that is, with a pixel matrix.

5. The method according to claim 1, wherein said at least one event consists in the presence of a character or sequence of characters or a graphic form relating to a specific situation of said diagnostic investigation or surgery, and said treatment provides for activation of a visual and/or acoustic signaling procedure of the occurrence of said at least one event, and/or of the memorization of a temporal reference to said at least one event, in synchronism with the memorization of the sequence of successive frames.

6. A system for identification and treatment of one or more events in a system for synchronization and combined display of information relating to progress of a diagnostic investigation or surgery performed on a patient, the information consisting of output signals coming from electromedical instruments and equipment (2a, 2b, 2c, . . . 2n), wherein the progress of the diagnostic investigation or surgery relates to at least one physiological parameter of said patient, or to images or videos taken during said diagnostic investigation or surgery, said system (100) comprising video signal derivative means (4a, 4b, 4c, . . . 4n), for deriving said image or video and providing derived output signals; a central unit (1) for collecting, processing and displaying the derived output signals; a processing program, operating in said central unit (1), comprising procedures for processing, displaying and storing said derived output signals; and acquisition means in said central unit, responsive to the derived output signals for cooperating with said processing program to make the derived output signals available for display in combined form in a monitor (7) of said central unit (6) as a sequence of successive frames suitable for constituting a continuous film or video, and for storage of the successive frames in the central unit (1);

wherein said system for identification and treatment comprises computer program procedures for executing, on each frame belonging to said sequence of successive frames, or belonging to at least a predefined set of frames of said sequence of successive frames, of the following operating phases:

searching in said frame, for identifying occurrence of the one or more events comprising presence of a character or sequence of characters, or a graphic form, wherein examples of said character or sequence of characters or graphic form are stored in an archive in the central unit (1), said searching carried out by comparing an identified occurrence of the one or more events and sought events for recognizing the identified occurrence as an occurrence of a sought event, the sought event comprising at least one of said one or more events stored in the archive;

executing, in case of recognition of at least one event, for each recognized event, a program procedure for a computer for carrying out a treatment on said frame and/or the activation of a program procedure for a computer for signaling the occurrence of said at least one event; and storing information relating to said at least one event, and/or a frame containing said at least one event, with a temporal reference with respect to the sequence of successive frames, wherein said at least one event consists in personal data of the patient, and said treatment comprises generating a mask (20) covering an area of said frame which includes the personal data, in order to obtain in the monitor (7) a corresponding masked frame, said storing carried out while keeping said masked frame a correct position in time within a temporal sequence with respect to the sequence of successive frames.

7. The system according to claim 6, wherein, if in said monitor (7) the area containing the personal data is moved and/or resized in one or more successive frames by a procedure of said processing program, said procedure also moves and/or consequently resizes said mask (20) in masked frames, to keep the area with personal data covered.

8. The system according to claim 6, wherein said processing program also stores a copy of a corresponding derived output signal comprising said personal patient data, and that said covering mask (20) is also generated and stored in the sequence of successive frames relating to the corresponding derived output signal.

9. The system according to claim 6, wherein the searching for said at least one event that consists in personal data is carried out by an OCR or character recognition procedure in a file of the "raster" type, that is, with a pixel matrix.

10. The system according to claim 6, wherein said at least one event consists in the presence of a character or sequence of characters or a graphic form relating to a specific situation of said diagnostic investigation or surgery, and said treatment provides for activation of a visual and/or acoustic signaling procedure of the occurrence of said at least one event, and/or of the memorization of a temporal reference to said at least one event, in synchronism with the memorization of the sequence of successive frames.

* * * * *